United States Patent [19]

Sheridan

[11] 4,349,725
[45] Sep. 14, 1982

[54] AIR DISPERSING HEAD FOR AIR HEATERS

[76] Inventor: John J. Sheridan, 2751 Virginia St., Shreveport, La. 71103

[21] Appl. No.: 159,614

[22] Filed: Jun. 16, 1980

[51] Int. Cl.³ .............................................. H05B 1/00
[52] U.S. Cl. .................................... 219/373; 219/367; 219/370; 433/32
[58] Field of Search .................... 433/32, 80; 219/373, 219/369, 370, 367; 128/257, 256; 239/128, 135

[56] References Cited

U.S. PATENT DOCUMENTS

| 1,771,366 | 7/1930 | Wyss et al. | 219/373 |
| 1,869,737 | 8/1932 | Breuer | 219/373 |
| 2,096,023 | 10/1937 | Albertson | 219/373 |
| 3,254,646 | 6/1966 | Staunt et al. | 128/257 |
| 3,612,824 | 10/1971 | Berryman et al. | 219/367 |
| 3,857,016 | 12/1974 | Meyer et al. | 219/373 |

FOREIGN PATENT DOCUMENTS 599521 7/1934 Fed. Rep. of Germany ...... 128/257
2708581 8/1978 Fed. Rep. of Germany ...... 219/370

Primary Examiner—Gene Mancene
Assistant Examiner—John J. Wilson

[57] ABSTRACT

An air dispersing head for an air heater which includes a generally cylindrically-shaped cap having an inset or recess on one side and fitted with a nozzle base and nozzle in the recess, with the nozzle communicating with the interior of the cap. The nozzle is fitted with a hose of selected length and the cap is further provided with a primary air duct and a plurality of secondary air ducts in a curved rear face oppositely disposed from the nozzle. Air is forced through the bottom of the air heater by an internally located fan, and is heated by coils, channelled through the air dispersing head and ejected from the hose. Unheated, ambient air enters the air dispersing head through the primary and secondary air ducts and mixes with the heated air to control the temperature of the air ejected from the end of the hose.

4 Claims, 6 Drawing Figures

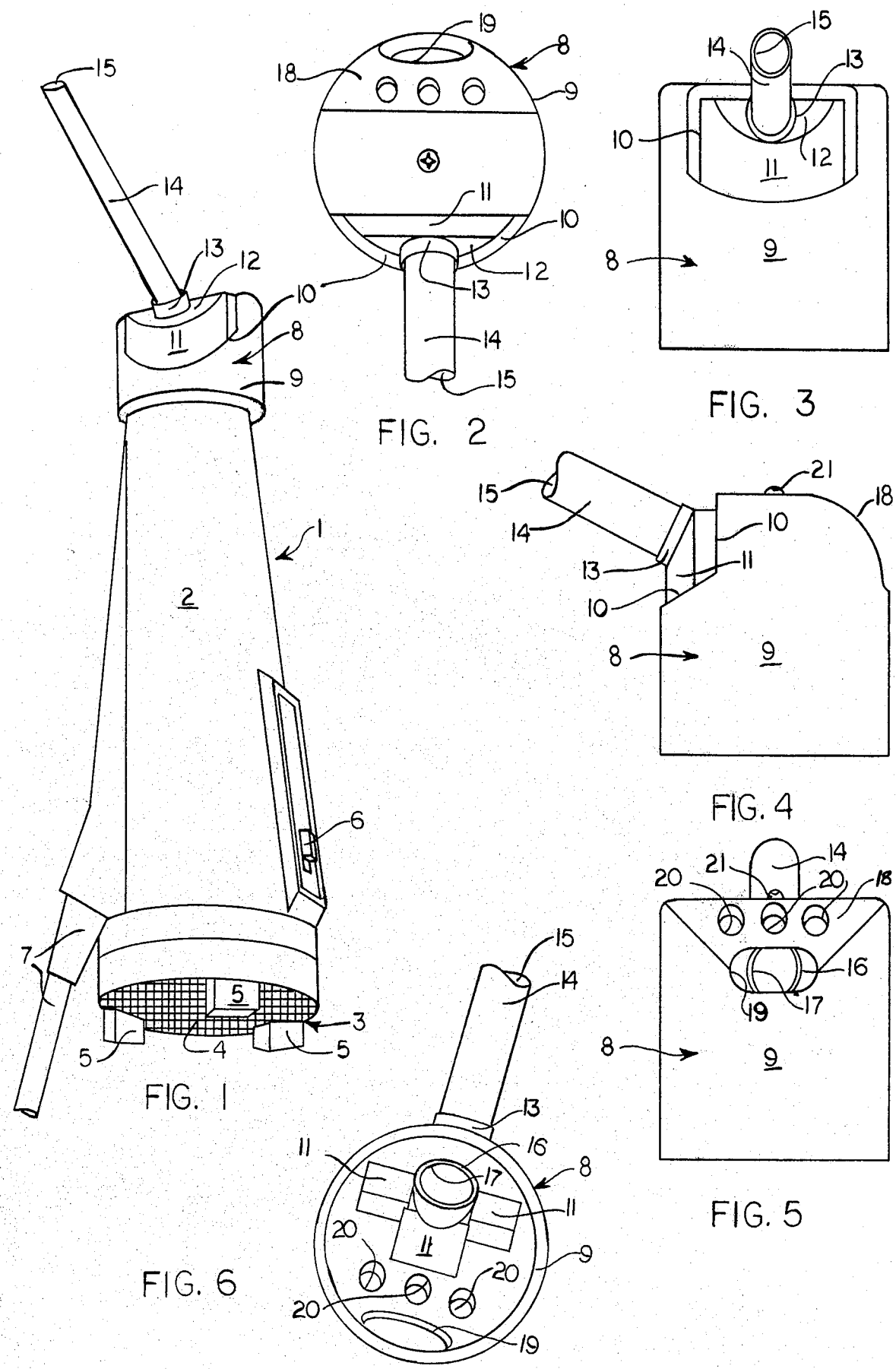

AIR DISPERSING HEAD FOR AIR HEATERS

BACKGROUND OF THE INVENTION

1. Field of the Invention

This invention relates to a means for providing a concentrated stream of high quality, oil and moisture-free air at a desirable temperature to a selected surface, and more particularly, to an air dispersing head for use with an air heater to supply warm air in orthodontic and dental applications. The air dispersing head of this invention is particularly well suited for supplying a controlled, concentrated stream of warm, high quality air to the teeth of a patient in orthodontic operations such as enamel bonding. The oil and water-free air stream can be directed on a single tooth or a group of teeth, and the temperature of the air can be closely and effectively controlled during use by simply controlling the volume of secondary or cool ambient air introduced into the dispersing head for blending with the heated air. The air heater and air dispersing head can be easily held and manipulated in one hand by either the doctor or patient to insure optimum curing conditions for the adhesive used in the orthodontic bonding or other procedure. The air dispersing head of this invention has been specifically designed for use with an air heater marketed by the Wahl Clipper Corporation under the trademark "Thermal Spot", but can be designed for use with substantially any air heater or blower according to design principals set forth hereafter.

1. Description of the Prior Art

Heat application techniques in the dental and orthodontic professions have varied according to the ingenuity of the indivdiual users. The majority of devices utilized have evolved as hair dryers or similar devices modified or adapted for the purpose of applying heated air to a tooth or teeth to cure the adhesive in detnal repair work and in other dental and orthodontic applications where such heat application is necessary. These devices are generally unsatisfactory in several particulars, icluding the application of a stream of air too large to facilitate accuracy, and having a temperature either too high for patient comfort, or too low to be effective in achieving the necessary results. Furthermore, the prior art air heating devices generally must be used and manipulated by the dentist or doctor, rather than by the patient, thus requiring the expenditure of additional time to complete the procedure. The devices used must also supply oil and moisture-free air, a requirement which generally eliminates conventional compressor systems, unless expensive filtering devices are employed.

Accordingly, it is an object of this invention to provide a new and improved air dispersing head for air heaters which includes an air dispersing nozzle and hose, and a plurality of apertures in the cap or shell for selective introduction of secondary or cool air into the head for mixing with the heated air supplied from the air heater, in order to closely control the temperature of the high quality, oil and moisture-free air in a concentrated stream to the work area.

Another object of the invention is to provide an air dispersing head or cap for use in cooperation with hand-held air heaters, which includes a generally cylindrically-shaped cap having a hollow interior and a nozzle communicating with the hollow interior, and further characterized by a plurality of apertures also communicating with the hollow interior of the cap to facilitate controlled entry of outside air into the hollow interior of the cap for mixing with hot air produced by the air heater and discharged into the air dispersing head.

Still another object of the invention is to provide an air dispersing head for use with air heaters, which includes a generally cylindrically-shaped cap having a discharge nozzle and a primary air duct in oppositely disposed relationship to the discharge nozzle, and further characterized by a plurality of secondary air ducts in close proximity to the primary air duct and in spaced relationship to each other in order to permit manual control of the air temperature exiting the head through the nozzle by blocking one or more of the secondary air ducts to control the quantity of cool, ambient air entering the head and mixing with the warm air generated by the air heater.

SUMMARY OF THE INVENTION

These and other objects of the invention are provided in an air disbursing head for use with air heaters which includes a generally cylindrically-shaped, hollow cap having a nozzle and hose combination for discharging heated air produced by the air heater when the head is secured to the air discharge of the heater. The head is further characterized by a primary air duct positioned in the cap in oppositely-disposed relationship with respect to the nozzle, and a plurality of secondary air ducts provided in spaced relationship near the primary air duct for controlling the quantity of cool air introduced into the air dispersing head for blending with the heated air discharged into the head by the air heater, with the primary object of closely controlling the temperature of the air ejected from the nozzle and hose attached to the head.

BRIEF DESCRIPTION OF THE DRAWING

The invention will be better understood by reference to the accompanying drawing, wherein:

FIG. 1 is a perspective view of an air heater and the air dispersing head of this invention mounted on the heater;

FIG. 2 is a top elevation of the air dispersing head illustrated in FIG. 1;

FIG. 3 is a front elevation of the air dispersing head illustrated in FIG. 1;

FIG. 4 is a side elevation of the air dispersing head illustrated in FIG. 1;

FIG. 5 is a rear elevation of the air dispersing head illustrated in FIG. 1; and FIG. 6 is a bottom view of the air dispersing head illustrated in FIG. 2-5.

DESCRIPTION OF THE PREFERRED EMBODIMENTS

Referring now to FIG 1 of the drawing, the air dispersing head of this invention is generally indicated by reference numeral 8, and is fitted to the top of air discharge of an air heater 1. Air heater 1 is characterized by a tapered, round shell or housing 2, and is provided with an air intake 3 at the bottom, covered by an intake screen 4. Legs 5 serve to support air heater 1 when it is placed on a flat surface, and a switch 6 serves to control the flow of electric current through electric cord 7 to drive the fan motor and heater (not illustrated) located inside housing 2.

Referring to FIGS. 1, 3, 4 and 5, air dispersing head 8 is characterized by a generally cylindrically-shaped body 9, provided with a body inset or window 10, to which is fitted a removable nozzle base 11. Nozzle base 11 is maintained in position in body inset 10 by means of a nozzle base screw 21, which extends through the top of body 9 and threadably into nozzle base 11. Nozzle base 11 is shaped to provide a flat nozzle face 12, the plane of which is fixed in angular relationship to the top of body 9. To this nozzle face 12 is affixed a nozzle 13, having a nozzle aperture 17, more particularly illustrated in FIG. 6, which communicates with the hollow interior of air dispersing head 8. A hose 14 of selected length is secured inside nozzle aperture 17 by means of a hose clamp 16, as further illustrated in FIGS. 5 and 6. The hose 14 may have a wall thickness of selected size to define a hose aperture 15 of different diameter to direct a stream of heated air to a work area of selected size. For example, if work is to be accomplished by a dentist or orthodontist on a specific tooth, the hose aperture 15 of the chosen hose 14 might be somewhat smaller than the hose selected if several teeth are to be considered in one procedure, where the work area is expanded. It will be understood that multiple nozzle bases 11, each having a hose 14 of varying internal diameter may be used with a common air dispersing head 8, according to the size of the work are envisioned. Alternatively, multiple hoses 14 can be provided in multiple air dispersing heads 8, as desired, to accomplish the same purpose.

Referring now to FIGS. 2, 5 and 6 of the drawing, the air dispersing head of this invention is provided with both a primary air duct 19 and multiple secondary air ducts 20, in the rear face 18 thereof. Primary air duct 19 is designed to provide cool, ambient air access to the interior of body 9 in order to permit blending and mixing of the cool air with hot air moving through air heater 1. The resulting air mixture is discharged from air dispersing head 8 through nozzle 13 and hose 14. The multiple secondary air ducts 20 are, in a preferred embodiment of the invention, aligned in spaced relationship above primary air duct 19 in rear face 18 of body 9. Accordingly, as air is forced through air intake 3 of air heater 1, and is heated and discharged into body 9 of air dispersing head 8, cool air enters primary air duct 19 and secondary air ducts 20, and mixes with the heated air to lower the temperature of the heated air. Selected ones of secondary air ducts 20 can therefore be blocked, individually or in combination, to regulate the temperature of the air discharging from hose 14 and onto the chosen work area. Furthermore, the air ducts or duct 20 selected for blockage can be temporarily closed by application of a small piece of tape or even by the user's finger or fingers as the air heater is manipulated to direct the stream of air on the work area. Finger manipulation to control air temperature at the hose 14 is particularly advantageous since a close control of the air temperature is possible by simply covering one or more of the secondary air ducts, as deemed necessary. For example, under circumstances where the primary air duct 19 is about 11/16 of an inch long and ⅜ of an inch wide, and three secondary air ducts 20, each having a diameter of about 3/16 of an inch are provided in rear face 18, and all air ducts are open, the air discharge temperature exiting hose 14 at a distance of about two inches from the end of the hose is about 65° centegrade. When one of the secondary air ducts 20 is blocked, the air temperature rises to about 70° centegrade, and a 5° rise is noted for each one of the other secondary air ducts 20 which is blocked. Blockage of all three secondary air ducts results in an air discharge temperature of about 85° centegrade. It will therfore be appreciated that a close temperature control of the air discharged from hose 14 can be achived by blocking one or more of the secondary air ducts 20 provided in body 9 of air dispersing head 8.

Referring again to FIGS. 2 and 5 of the drawing, it will be appreciated that substantially any number of secondary air ducts 20 can be provided in rear face 18 of body 9. However, in a preferred embodiment of the invention a total of three such ducts are provided, and in a most preferred embodiment, for an air dispersing head having a diameter of about 1⅜ inches and a height of about 1½ inches, each of the three secondary air ducts 20 should have a diameter of about 3/16 of an inch, where the primary air duct 19 is about 11/16 of an inch wide and 5/16 of an inch high. This latitude in temperature adjustment permits an exit air temperature range of from about 65° centegrade to about 85° centegrade by blocking none to all three of the secondary air ducts, respectively.

It will be appreciated by those skilled in the art that while the air dispersing head of this invention has been specifically designed for use with the "Thermal Spot" air heater illustrated in FIG. 1 of the drawing, in order to control the temperature of the air ejected from the hose 14, a similar head can be used on air heaters of substantially any design for the same purpose. Accordingly, regardless of the shape and size of air dispersing head 8, multiple secondary air ducts 20 can be provided to facilitate controlled mixing of ambient air with the heated air produced by the air heater to produce air having a selected temperature to accomplish the desired results.

Having described my invention with the particularity set forth above, what is claimed is:

1. An air dispersing head for an air heater comprising:
   (a) a generally cylindrically-shaped cap means shaped for cooperation with the air discharge of said air heater and having an internal cavity and a primary air duct for introduction of ambient air into said cavity;
   (b) hose means extending through said cap means on a side of said cap means opposite said primary air duct and into said cavity for directing heated air from said heater to a work area; and
   (c) a plurality of secondary air ducts in said cap means and located on the same side of said cap means as said primary air duct for controlling a secondary flow of ambient air into said cavity and adjusting the temperature of said heated air discharged from said hose means.

2. The air dispersing head of claim 1 wherein said primary air duct is larger than each of said secondary air ducts.

3. The air dispersing head of claim 1 wherein said plurality of secondary air ducts is three secondary air ducts in spaced relationship in said cap means and positioned above said primary air duct, and sized with respect to said primary air duct and said cavity to effect about a 5° centigrade temperature drop in said heated air discharged from said hose means for each of said secondary air ducts which are open.

4. The air dispersing head of claim 1 wherein:
   (a) said primary air duct is larger than each of said secondary air ducts; and
   (b) said plurality of secondary air ducts is three secondary air ducts in spaced relationship in said cap means and positioned above said primary air duct and sized with respect to said primary air duct and said cavity to effect about a 5° centigrade temperature drop in said heated air discharged from said hose means for each of said secondary air ducts which are open.

* * * * *